United States Patent [19]

Yeh

[11] Patent Number: 5,350,670

[45] Date of Patent: Sep. 27, 1994

[54] COMPOSITION FOR PRESERVING NON-LIVING ANIMAL BODIES

[76] Inventor: Tso-Li Yeh, 8F-3, No. 68, Cheng-Yih N Road, San-Chung, Taiwan

[21] Appl. No.: 913,354

[22] Filed: Jul. 15, 1992

[51] Int. Cl.[5] .......................... A01N 1/02; A01N 1/00
[52] U.S. Cl. ......................................... 435/1; 27/21.1; 27/22.1; 27/22.2; 424/75
[58] Field of Search .................... 424/75; 435/1; 8/94.19 R; 434/296; 27/21.1, 22.1, 22.2

[56] References Cited

U.S. PATENT DOCUMENTS

| | | | |
|---|---|---|---|
| 81,185 | 8/1868 | Lugo | 27/22.2 |
| 3,780,452 | 12/1973 | Jackson | 35/20 |
| 3,912,809 | 10/1975 | Rendon | 424/75 |
| 4,224,029 | 9/1980 | Heinz | 8/94.19 R |
| 4,502,859 | 3/1985 | Knobloch | 8/94.29 |
| 4,675,327 | 6/1987 | Fredrick | 514/383 |

FOREIGN PATENT DOCUMENTS 6095 of 1913 United Kingdom ................. 27/22.2

OTHER PUBLICATIONS

Barnes, C. S., The Art & Science of Embalming, 9th Ed. 1906, pp. 373–382.

*Primary Examiner*—Michael G. Wityshyn
*Assistant Examiner*—Ralph Gitomer
*Attorney, Agent, or Firm*—Bacon & Thomas

[57] ABSTRACT

This invention relates to a composition for preserving animals as specimens. The composition is a three-in-one composition which is prepared by combining Formaldehyde Solution and Alcohol with particles made from Boric Acid, NaCl and Phenol, and it not only soaks and hardens animals entirely, but it also simplifies the process of production by avoiding the procedures of removing skeleton, muscle and internal organs from an animal carcass.

18 Claims, No Drawings

COMPOSITION FOR PRESERVING NON-LIVING ANIMAL BODIES

FIELD OF THE INVENTION

This invention relates to a composition for preserving animal bodies. The said composition consists of Boric Acid, NaCl, Phenol, Formaldehyde Solution, Alcohols and pre-ground particles of Boric Acid, NaCl, and Phenol. This three-in-one composition can totally harden the specimen without the procedures of removing the skeleton, muscle and internal organs from the animal carcass, thus simplifying the process of preserving animal bodies as specimens.

BACKGROUND OF THE INVENTION

In traditional specimen-making, with poor effect but high cost, a dog for example, to be preserved would have to have its internal organs removed from its body, as well as its skeleton and muscle, with only the fur remaining. The remaining furs are then preserved before being filled with paste and cotton cloth. After these stages, the cuts are sewn up and the dog's pose is fixed with iron wires. The specimen is finished when the dog's furs are finally dried. Observing the whole processes of specimen-making, we know it is so complicated that only the professionals can do it. Besides, it needs comprehensive applied tools and medicines for use in its processes. Thus, conventional methods are not only expensive but are also difficult. Therefore we have invented a three-in-one composition through continual research and experiments in order to overcome traditional faults. The ingredients of the creative composition include Boric Acid, NaCl, Phenol, Formaldehyde Solution and Alcohols. Mixing them up according to specified proportions will produce a kind of solution which may be used to preserve an animal or plant specimen.

SUMMARY OF THE INVENTION

The main purpose of the present invention is that the composition both for animal and plant specimen-making is a preserving composition which can penetrate materials and soak the animals or plants directly, thus simplifying the procedures of specimen-making.

Another purpose of the present invention is that the preserving composition mentioned above can preserve the muscle, skeleton and internal organs very well for future research.

DETAILED DESCRIPTION OF THE INVENTION

For an understanding of the effect of the invention, we would describe the results obtaining from experiments as follows:

The innovative composition which is prepared for the making of animal or plant specimens is a combination of three different formulas which are designated as A, B, and C respectively. Formula A is made from 10 g 100% Boric Acid, 150 g NaCl and 30 g Phenol, which should be ground into particles at first with the proportion of 1:15:3 (Boric Acid:NaCl:Phenol). Formula B is made from 5 L 35% Formaldehyde Solution. Formula C is made from 5 L 98% Alcohols. To make the composition, formulas A, B, and C are to be mixed in a proportion of 1:1:1 at first. Formula C is first added to a vessel. Formula B is then added to the vessel, followed by Formula A, and the mixture is allowed to sit for ten minutes. The mixture is then stirred violently until it is wholly dissolved and the final composition is done. (When pouring formula A into the vessel, it should be poured slowly.)

To make the specimen, the material to be preserved should be weighed after it is washed thoroughly in order to calculate the needed time for soaking, which can be calculated according to the formula: every kilo needs 36 hours' soaking in the three-in-one composition (this is an average formula which can be changed depending on the size of the material). After the needed time is calculated, the material is immersed in the composition entirely and is allowed to soak for the calculated time. When the time is up, the material is removed for shaping and drying and the specimen is made.

Because the pores of an animal will close after it is dead, the composition can not penetrate them to preserve the animal as a specimen. Thus, formula A is used to open the pores to permit entry of formula A, B, C. Formula C, which can vaporize, can be used to expel formula A and B out of the carcass after hardening. The carcass will become hardened after it contacts with formula A, B, and C, which affects enzymes and contacts with muscle; therefore, the composition degrades chemical organization and thus produces an enzymatic effect.

There are three stages during which the carcass becomes hardened. The first stage takes 10 days for the skeleton to get hardened, but muscle won't harden during this stage; it is still flexible. The second stage takes another 10 days for skeleton and joint organizations to become hardened. The third and last stage takes the other 10 days for the whole carcass to become hardened and all of the pores to close. A finished specimen is thus produced.

The following are two experiments using the innovative composition:

Experiment A: Specimen of Dog

One dead dog weighed at 610 g; 2 L three-in-one composition; a 3 L capped can; a pair of plastic gloves; and 150 cm thin iron wires are required for the making of specimen. The three-in-one composition is first poured into the can and then stirred to the proper state. Secondly, the carcass of the dog is placed into the 3 L can and totally immersed in the composition, after is has been fixed with the iron wires. Then, the cap is put on and allowed to sit for three weeks. When three weeks have passed, the carcass is taken out and the wires are released. The carcass is allowed to dry and harden in a shady place (to become hardened requires about one month through the three stages mentioned above). After the carcass is totally hardened, the eyes are removed and replaced with false ones.

During the process of specimen-making, the weight of the carcass changes at different phases. Its original weight is 610 g and will increase to 830 g after soaking. It will decrease to 740 g after it is dried for one week; to 630 g after two weeks of drying, It becomes 520 g, 465 g, 464 g at the first, second, and third months. In addition, its colors and nails won't come off and its muscle is flexible. It is also washable even if it is exhibited for a long time.

Experiment B: Specimen of Fish

One dead fish weighed at 625 g; 2 L three-in-one composition; 3 L capped can; and a pair of plastic gloves are obtained for the making of specimen. The carcass of the fish is first placed inside the 3 L can and is entirely immersed in the composition for 12 days. When 12 days have passed, the fish is removed and cleaned, after which its pose is adjusted, before it is dried and hardened in a shady place. After the carcass totally hardens, its eyes are removed and replaced with false ones. Then a specimen is made. The weight of the carcass also changes at different times. Its original weight is 625 g, which increases to 710 g after soaking; decreases to 680 g one week after soaking; and decreases to 575 g three weeks later. Its weight at first, second, third month are respectively 420 g, 415 g, and 412 g. Likewise, its color and other pieces won't come off after long time exposure and its muscle is flexible. The specimen is also washable.

In a summary, this innovative three-in-one composition which avoids the procedures of removing skeleton, muscle and internal organs of the carcass, and thus simplifies the processes of specimen-making, is able to well preserve the original color and flexibility of the animal or plant and have the carcass totally hardened. It makes specimen-making more convenient and has valuable utilities.

I claim:

1. A composition for preserving non-living animal bodies comprising:
   A) a particulate mixture of 100% boric acid, NaCl and phenol;
   B) formaldehyde; and
   C) alcohol
   wherein the components A, B and C are present in a ratio of 1:1:1 by weight.

2. A composition according to claim 1 wherein the formaldehyde is 35% by weight formaldehyde and the alcohol is 98% by weight alcohol.

3. A composition according to claim 1 wherein the mixture of boric acid, NaCl and phenol is an approximately 1:15:3 by weight mixture.

4. A composition according to claim 1 wherein the mixture of boric acid, NaCl and phenol is an approximately 1:15:3 by weight mixture.

5. A method for preserving a non-living animal body, without removal of muscle, skeleton or internal organs, which comprises:
   washing the animal body;
   immersing the animal body in a vessel with a preservative composition comprising a particulate mixture of 100% boric acid, NaCl and phenol, formaldehyde and alcohol, wherein the boric acid, NaCl an phenol of said mixture are present in a ratio of 1:1:1 for approximately 36 hours for each kilogram of body weight;
   removing the animal body from the preservative composition;
   shaping the animal body; and
   drying the animal body.

6. A method according to claim 5 wherein the formaldehyde is 35% by weight formaldehyde and the alcohol is 98% by weight alcohol.

7. A method according to claim 5 wherein the mixture of boric acid, NaCl and phenol is an approximately 1:15:3 by weight mixture.

8. A method according to claim 6 wherein the mixture of boric acid, NaCl and phenol is an approximately 1:15:3 by weight mixture.

9. A method according to claim 5 wherein the drying step takes at least 30 days.

10. A method according to claim 9 wherein the drying step takes place in a shaded area.

11. A composition for preserving non-living animal bodies comprising:
    A) a particulate mixture of 100% boric acid, NaCl and phenol;
    B) formaldehyde; and
    C) alcohol,
    wherein the components A, B and C are present in a ratio of 1:1:1, by weight and wherein the mixture of boric acid, NaCl and phenol is an approximately 1:15:3 by weight mixture.

12. A composition according to claim 11 wherein the formaldehyde is 35% by weight formaldehyde and the alcohol is 98% by weight alcohol.

13. A method for preserving a non-living animal body, without removal of muscle, skeleton or internal organs, which comprises:
    washing the animal body;
    immersing the animal body in a vessel with a preservative composition according to claim 11 for approximately 36 hours for each kilogram of body weight;
    removing the animal body from the preservative composition;
    shaping the animal body; and
    drying the animal body.

14. A method for preserving a non-living animal body, without removal of muscle, skeleton or internal organs, which comprises:
    washing the animal body;
    immersing the animal body in a vessel with a preservative composition according to claim 12 for approximately 36 hours for each kilogram of body weight;
    removing the animal body from the preservative composition;
    shaping the animal body; and
    drying the animal body.

15. A method according to claim 13 wherein the drying step takes at least 30 days.

16. A method according to claim 14 wherein the drying step takes at least 30 days.

17. A method according to claim 15 wherein the drying step takes place in a shaded area.

18. A method according to claim 16 wherein the drying step takes place in a shaded area.

* * * * *